United States Patent [19]

Matson et al.

[11] Patent Number: 6,051,740

[45] Date of Patent: Apr. 18, 2000

[54] OXIDATION OF MERCAPTANS TO DISULFIDES

[75] Inventors: Michael S. Matson; Harold J. Swindell, both of Bartlesville, Okla.

[73] Assignee: Phillips Petroleum Company, Bartlesville, Okla.

[21] Appl. No.: 09/210,034

[22] Filed: Dec. 11, 1998

[51] Int. Cl.[7] .................................................. C07C 319/14
[52] U.S. Cl. .................................................. 568/59; 568/38
[58] Field of Search .................................. 568/21, 25, 26, 568/36, 38, 39, 59

[56] References Cited

U.S. PATENT DOCUMENTS

| | | | |
|---|---|---|---|
| 2,503,644 | 4/1950 | Warner | 568/26 |
| 2,517,934 | 8/1950 | Schulze | 568/26 |
| 2,558,221 | 6/1951 | Mertz | 568/26 |
| 2,656,392 | 10/1953 | Schulze | 568/26 |
| 2,790,008 | 4/1957 | Warner | 568/26 |
| 2,792,334 | 5/1957 | Meguerian | 568/26 |
| 2,859,249 | 11/1958 | Haimsohn et al. | 260/608 |
| 3,022,351 | 2/1962 | Mihru et al. | 260/608 |
| 3,294,760 | 12/1966 | Hay | 528/374 |
| 3,565,959 | 2/1971 | Takase | 568/25 |
| 3,755,461 | 8/1973 | Kyasnikoff et al. | 260/608 |
| 4,277,623 | 7/1981 | Kubicek | 568/26 |
| 4,288,627 | 9/1981 | Kubicek | 568/26 |
| 4,302,605 | 11/1981 | Buchholz et al. | 568/60 |
| 4,868,336 | 9/1989 | Presnall | 568/25 |
| 5,202,494 | 4/1993 | Roberts et al. | 568/26 |
| 5,530,163 | 6/1996 | Shaw | 568/26 |

OTHER PUBLICATIONS

Kirk–Othmer Encycl. Chem. Technol., vol. 22, pp. 946–964 (1982).

*Primary Examiner*—Gary Geist
*Assistant Examiner*—Jean F Vollano
*Attorney, Agent, or Firm*—Richmond, Hitchcock, Fish & Dollar

[57] ABSTRACT

A process which can be used to produce an organic disulfide is provided. The process comprises contacting a mercaptan in the presence of an oxygen-containing fluid, a catalyst, optionally a cocatalyst, and further optionally a solvent or a surfactant or combination of a solvent and surfactant under a condition sufficient to oxidize the mercaptan to an organic disulfide.

21 Claims, No Drawings

OXIDATION OF MERCAPTANS TO DISULFIDES

FIELD OF THE INVENTION

The invention relates to a process for producing organic disulfides by oxidation of mercaptans.

BACKGROUND OF THE INVENTION

Organic disulfides are useful chemicals for pre-sulfiding catalysts and as chemical intermediates in the production of agricultural and pharmaceutical products. Organic disulfides are produced by oxidation of mercaptans according to the general reaction $$2R\text{—}SH + \text{Oxidant} \rightarrow R\text{—}S\text{—}S\text{—}R + \text{Reductant} \quad (1)$$

The most common oxidants for consideration are sulfur, hydrogen peroxide, a reducible metal ion, and oxygen. Examples of these are as follows:

$$2R\text{—}SH + S \rightarrow R\text{—}S\text{—}S\text{—}R + H_2S \quad (2)$$

$$2R\text{—}SH + H_2O_2 \rightarrow R\text{—}S\text{—}S\text{—}R + 2H_2O \quad (3)$$

$$2R\text{—}SH + 2Fe^{+3} \rightarrow R\text{—}S\text{—}S\text{—}R + 2Fe^{+2} + 2H^+ \quad (4)$$

$$2Fe^{+2} + O_2 + 2H^+ \rightarrow 2Fe^{+3} + H_2O \quad (5)$$

$$2R\text{—}SH + O_2 R\text{—}S\text{—}S\text{—}R + H_2O \quad (6)$$

In order to minimize production of polysulfides, when sulfur is used as oxidant, excess mercaptan is used, generally in at least 50–100% excess. The mercaptan then needs to be recovered from the by-product hydrogen sulfide for recycle. Also, the disulfide must be recovered from the polysulfides formed.

The use of hydrogen peroxide suffers from the production of 2 moles of water per mole of disulfide produced as well as the additional water present with the aqueous solution of hydrogen peroxide. Thus, the reactor volume productivity is low for this method.

The use of stoichiometric amount of metal ion such as ferric nitrate is a possibility (reaction 4). However, this process also suffers from low volume productivity of disulfide produced per reactor volume. The advantage is that the ferrous ion can be regenerated with air to produce ferric ion (reaction 5).

The other alternative is to use oxygen as the oxidant. This reaction can achieve high conversions (>99.5%) with high selectivity (>98%). The reactions are done in the presence of a basic catalyst, such as caustic, triethylamine or phase transfer catalysts such as TERGITOL®. Based on reaction (4), it is anticipated that metal ions can serve as co-catalysts for the oxidation of mercaptans.

The use of oxygen does have a significant potential safety issue due to the potential for explosions under certain conditions. The production of the lower alkyl sulfides such as, for example, dimethyl disulfide poses an additional concern due to the high partial pressure of methyl mercaptan. It has been experimentally shown that, at the pressure of 400 psig and temperature of 50° C. used in the production of dimethyl disulfide, 10 volume % oxygen is the lower explosive limit for methyl mercaptan. At concentrations higher than 10 volume % oxygen, there is a risk of explosion if there is an ignition source also present. For safety considerations, the reaction is performed under conditions where the oxygen concentration is kept to less than about 10 volume %, preferably less than 7 volume %, and most preferably less than 5 volume %. Therefore, there is a need to develop a process for oxidizing a mercaptan to an organic disulfide using oxygen in the safe region and achieving the highest possible yield of disulfide.

SUMMARY OF THE INVENTION

An object of the invention is to provide a process for producing organic disulfides. An advantage of the invention is that the invention process for oxidizing mercaptan is carried out under substantially a reduced risk of, or free of, explosion. Other advantages of the invention include a high volume productivity, no production of excessive by-products, and no requirement of regeneration of the oxidant used in the process. Other objects and advantages will become more apparent as the invention is more fully disclosed hereinbelow.

According to the invention, a process which can be used to produce an organic disulfide is provided. The process can comprise, consist essentially of, or consists of contacting a mercaptan in the presence of an oxygen-containing fluid, a catalyst, optionally a cocatalyst, and further optionally a solvent or a surfactant or combination of a solvent and surfactant under a condition sufficient to oxidize the mercaptan to an organic disulfide.

DETAILED DESCRIPTION OF THE INVENTION

According to the invention, the term "fluid" refers to liquid, gas, vapor, or combinations of two or more thereof. The term "substantial" or "substantially" signifies that which is more than trivial. Any oxygen-containing fluid can be used in the invention. Examples of oxygen-containing fluids include, but are not limited to, liquid oxygen, gaseous oxygen, liquid air, gaseous air, or combinations of two or more thereof.

Any mercaptans having the formula of RSH can be used. In the formula, R is a hydrocarbyl radical having 1 to about 20, preferably 1 to about 15, and most preferably 1 to 12 carbon atoms per radical. The radical can be alkyl, aryl, alkenyl, cycloalkyl, or combinations of two or more thereof. Each radical can contain one or more substituents such as, for example, hydroxy, amino, halo, carbonyl, or combinations of two or more thereof.

Examples of mercaptans include, but are not limited to, methyl mercaptan, ethyl mercaptan, propyl mercaptan, isopropyl mercaptan, butyl mercaptan, isobutyl mercaptan, sec-butyl mercaptan, tert-butyl mercaptan, pentyl mercaptan, isoamyl mercaptan, pentane-3-thiol, hexyl mercaptan, isohexyl mercaptan, thiophenol, benzyl mercaptan, nonyl mercaptan, tert-dodecyl mercaptan, and combinations of two or more thereof. The presently preferred mercaptans are the lower alkyl mercaptans such as, for example, methyl mercaptan.

Organic disulfide produced in the oxidation of mercaptan is the corresponding disulfide of the mercaptan. For example, methyl mercaptan is oxidized to dimethyl disulfide.

Any catalyst which can catalyze the oxidation of a mercaptan can be used in the invention. The presently preferred catalyst is a basic catalyst.

According to the present invention, the basic catalyst can be any base. The presenting preferred base can be an inorganic base, an organic base, or combinations of two or more thereof. Suitable organic bases include, but are not limited to, methyl amine, dimethyl amine, trimethyl amine, ethyl amine, diethyl amine, triethylamine, propyl amine, isopropyl amine, dipropyl amine, diisopropyl amine, tripropyl amine, butyl amine, tributyl amine, amyl amine, triamyl amine, hexyl amine, cyclohexyl amine, octyl amine, piperidine, pyrrolidine, morpholine, dimethylethanol amine, tetramethylammonium hydroxide, tetraethylammonium hydroxide, tetrapropylammonium hydroxide, and combinations of two or more thereof. Suitable inorganic bases include, but are not limited to, lithium hydroxide, sodium hydroxide, sodium hydrosulfide, sodium bisulfide, potassium hydroxide, calcium hydroxide, magnesium hydroxide, sodium bicarbonate, sodium carbonate, sodium oxide, sodium sulfide, magnesium oxide, calcium oxide, calcium carbonate, sodium phenoxide, barium phenoxide, calcium phenoxide, partially neutralized acids in which one or more protons of an acid is replaced with ammonium or metal ions, $R^1ONa$, $R^1OK$, $R^1SNa$ such as sodium methanethiolate, $R^1SK$, and combinations of two or more thereof; where $R^1$ is a $C_1$–$C_{18}$ alkyl radical, or combinations of two or more thereof. Among the bases, sodium hydroxide is preferred because it is readily available and inexpensive.

Any metal or metal compound that can increase reaction rate can be a cocatalyst. The presently preferred cocatalyst is a transition metal or a transition metal compound.

Examples of suitable co-catalysts include, but are not limited to, ferric chloride, ferric bromide, ferric sulfate, ferric nitrate, ferric phosphate, cobalt chloride, cobalt bromide, cobalt sulfate, cobalt nitrate, cobalt phosphate, nickel chloride, nickel bromide, nickel sulfate, nickel nitrate, nickel phosphate, copper chloride, copper bromide, copper sulfate, copper nitrate, copper phosphate, copper acetate, cobalt acetate, nickel acetate, copper naphthenate, cobalt naphthenate, nickel naphthenate, copper oxide, copper hydroxide, nickel oxide, nickel hydroxide, cobalt oxide, or combinations of two or more thereof.

A solvent or a surfactant which can increase the reaction rate of the mercaptan oxidation, or facilitate the phase separation of the disulfide from the product medium, or both can be used in the invention process wherein the product medium comprises unreacted mercaptan, spent catalyst, and the solvent or surfactant. Examples of suitable solvent include, but are not limited to, methanol, ethanol, propanol, isopropanol, acetone, methylethyl ketone, butanol, tetrahydrofuran, sulfolane, dimethyl sulfoxide, dimethyl disulfide, water, hexane, cyclohexane, toluene, dioxane, xylene, dimethyl sulfide, or combinations of two or more thereof.

According to the present invention, any surfactant that facilitates the mixing of reactants into substantially a single phase can be used. Generally, the surfactant comprises one or more compounds which exhibit surface-active properties. A preferred surfactant for use in the reaction system of the instant invention is selected from the group consisting of alkoxylated compounds, quaternary ammonium salts, alkali metal alkyl sulfates, alkali metal salts of alkanoic acids, alkali metal salts of alkaryl sulfonic acids, 1-alkyl pyridinium salts, and combinations of any two or more thereof.

The presently preferred surfactant is an alkoxylated compound. Examples of suitable alkoxylated compounds include, but are not limited to, alkoxylated alcohols, alkoxylated mercaptans, sulfates of alkoxylated alcohols, alkoxylated phenols, sulfates of alkoxylated phenols, and combinations of any two or more thereof.

An example of suitable alkoxylated alcohol is TERGITOL® 15-S-7 which is an ethoxylated alcohol, is manufactured and marketed by Union Carbide Corporation, and has the formula of $R^2O(CH_2CH_2O)_7H$ where $R^2$ is a secondary alkyl radical having 11–15 carbon atoms and 7 is the averaged number of the ethylene oxide units. Another example is an ethoxylated phenol having the same number of ethylene oxide units. Other suitable alkoxylated alcohols can also be available from Union Carbide Corporation.

Because the surfactants are well known to one skilled in the art, description of which is omitted herein for the interest of brevity.

According to the invention, the contacting of the oxygen-containing fluid is preferably carried out in the vapor phase. The oxygen content in the vapor phase of the mixture of the reactants and the oxygen-containing fluid is preferably kept from about 1 to about 10 volume percent, more preferably about 3 to about 8 volume %, and most preferably in the range of from about 5 to 7 volume %.

The amount of catalyst required is a catalytic amount that is sufficient to catalyze the oxidation of a mercaptan to its corresponding disulfide. Generally the amount can be in the range of about 0.0001 to about 10 weight percent, preferably about 0.001 to about 5 weight %, and most preferably 0.005 to 5 weight % of the reaction mixture which comprises the mercaptan, catalyst, and solvent, if present.

A co-catalyst can be present in the amount of about 0.001 to about 10 weight % of the catalyst employed. The weight % of metal in the catalyst, based the weight of mercaptan can generally be in the range of from about 0.00001 to about 1%, preferably about 0.0001% to about 0.01%.

According to the invention, the mercaptan can be present in the reaction mixture in the amount of about 30 to about 95 weight %, preferably about 40 to about 95 weight %, more preferably about 50 to about 95 weight %, even more preferably about 75 to about 95 weight %, and most preferably 85 to 95 weight %.

The solvent is present in an amount of about 1 to about 20 weight % based on the amount of mercaptan, preferably about 5 to about 15 weight %, and most preferably about 10 weight %.

As disclosed above, the contacting of the mercaptan and the oxygen-containing fluid is preferably carried out in the vapor phase in a suitable reaction vessel. The condition for the contacting is that which is sufficient to convert the mercaptan to its corresponding disulfide. Generally, the condition can include a temperature in the range of about 10 to about 200° C., preferably about 20 to about 150° C., more preferably about 30 to about 100° C., and most preferably 40 to 60° C.; a pressure in the range of from about 1 to about 100 atmospheres (atm), preferably about 10 to about 75 atm, more preferably about 20 to about 35 atm, and most preferably 25 to 30 atm; and a contacting time in the range of from about 0.05 to about 10 hours, preferably about 0.1 to about 5 hours, and most preferably 0.2 to 3 hours. It should be noted that the contacting can take substantially longer for substantially completing the oxidation of mercaptan, if the catalyst does not comprise a cocatalyst.

The contacting is carried out in the vapor phase, as disclosed above. The resulting oxygen-containing vapor is then mixed with the liquid phase by any means to one skilled in the art.

Once the oxidation of mercaptan is completed, a product medium is produced which, as disclosed above, includes an organic disulfide; unreacted mercaptan, if any; spent catalyst and/or cocatalyst; water; and solvent. The organic disulfide product is generally present in the organic phase of the medium and can be recovered and further purified, if desired, by any means known to one skilled in the art.

Following phase separation of the organic and aqueous phases, the presently preferred means is distillation because the cocatalyst can be readily removed as precipitate upon distillation. Catalyst and cocatalyst can be recovered by any means known to one skilled in the art and recycled to the reaction vessel for use, if desired. However, such recovery and recycle is not generally required.

A preferred embodiment of the invention relates to the production of dimethyl disulfide which is the primary focus of the process disclosed herein since it poses the greatest potential safety risk due to the greater volatility of methyl mercaptan relative to the other mercaptans. Although other mercaptans have been operated very successfully utilizing the process disclosed herein, methyl mercaptan is illustrated hereinbelow.

The process of this invention incorporates a reactor design that allows safe use of oxygen as well as a catalyst and solvent system that maximizes reactor productivity with minimum use of catalyst and solvent for the oxidation of methyl mercaptan to dimethyl disulfide and a separation scheme to obtain high purity dimethyl disulfide. The catalyst usage is minimized to the point that there is no economic incentive to recover and recycle it. The safe operation is obtained by introduction of oxygen into the vapor phase of the reactor such that the volume % of oxygen is kept below about 10%, preferably at about 5 volume %. Sufficient oxygen partial pressure is maintained on the reactor by operating the reactor at 400 psig of nitrogen at reactor temperature. Oxygen is introduced at a differential pressure of 20 psig. The oxygen is allowed to react with the mercaptan and catalyst in the liquid phase. The oxygen is transported to the liquid phase by having sufficient mixing such as, for example, an impeller operating at about 1000 revolutions per minute (rpm), a mixer in conjunction with a roll pump providing additional mixing, or a radial type mixer in conjunction with a liquid pump around loop and a vapor circulation loop. Oxygen is injected into the vapor phase and the vapor phase circulated to the suction of a wet gas compressor. The compressor moves the vapors (containing about 5 volume % oxygen) to sparge nozzles located at the bottom of the reactor. The reactors are also equipped with oxygen sensors in the vapor phase for monitoring oxygen concentration. Alarms and shut down devices are included in the design to halt oxygen addition in the event of high oxygen volume % in the vapor space, oxygen flow rate exceeds a predetermined rate, reactor pressure exceeds 430 psig or in the event of a sudden drop in reactor pressure. In the invention process, the catalyst and solvent system and methyl mercaptan are charged to the batch reactor. The temperature is raised to 30–70° C., preferably 50° C. and the pressure on the reactor raised to 400 psig with nitrogen. Oxygen is introduced into the vapor space and is transported to the liquid phase by sufficient mixing. Catalyst and solvent system enhance the reaction rate. The oxygen partial pressure has a direct effect on the reaction rate, the higher the partial pressure the faster the reaction. However, safety considerations dictate that the volume % of oxygen must be kept in the range disclosed above. For example, the reaction pressure of about 400 psig allows for an oxygen partial pressure of up to 20 psig while still maintaining the volume % of oxygen in the safe region.

The invention process also incorporates a minimum amount of catalyst to produce a steady reaction rate and in an amount that does not require the process to incorporate a complex or expensive recovery and recycle system for the catalyst. The invention process also uses a minimum amount of a solvent to enhance the reaction rate and to facilitate separation process.

The preferred catalyst for the invention process is a solution of caustic as a 20% solution of sodium hydroxide in water. Higher concentrations of caustic up to 50% can be used but the use of the lower concentration is preferred in commercial scale operation for handling reasons. The preferred amount of 20% caustic to be used in methyl mercaptan oxidation is 0.5 weight % to 2.5 weight % based on the weight of methyl mercaptan to be reacted. Although the reaction will proceed without caustic, the rate of oxygen uptake during the course of the reaction is variable, is very slow, and can be different from batch to batch.

The preferred cocatalyst is a copper salt for methyl mercaptan oxidation. It has been demonstrated that with caustic only as the catalyst, the reaction rate drops during the first several batches and will finally reach a slower reaction rate after several batches. The addition of the preferred copper cocatalyst results in a uniform reaction rate from batch to batch. The use of the copper co-catalyst also increases the reaction rate in each batch. Although other metal salts can also be used in the process such as salts of nickel, chromium, iron and cobalt, the preferred catalyst for dimethyl disulfide is copper. Cobalt, however, is preferred over copper for the production of dibutyl disulfide. The process for producing dimethyl disulfide is that the amount of metal present in the reaction medium or mixture is on the order of about 10 to about 100 ppm of metal on a weight basis of the total weight charged to the reactor. The metal catalysts can be in the form of the acetate, sulfate, nitrate, chloride, oxide, hydroxide or other suitable forms. For the purpose of this invention, copper in the form of cupric acetate or cupric sulfate as the hydrate are the preferred salts. The choice of salt is dictated by availability, cost, solubility and potential impact of the counter ion on the metallurgy. For example, chloride salts in aqueous systems are not compatible with stainless steel.

The oxidation of a mercaptan with oxygen is a multiphase system. At a minimum, there are two liquid phases and a gas phase. The two liquid phases are the aqueous phase of caustic and copper cocatalyst, and the methyl mercaptan phase. As the reaction progresses to form dimethyl disulfide, water is also formed, increasing the volume of the aqueous phase. As methyl mercaptan is reacted to produce the disulfide, the density of the organic phase increases.

When no solvent is present, the densities of the two final phases can be very similar and depends on the initial amount and concentration of the caustic phase. It is possible to have the phases invert or separate very poorly as the caustic amount and concentration changes relative to the amount of mercaptan charged and the final conversion achieved at the end of reaction. The invention process also eliminates this concern and at the same time improve the separation and recovery scheme by the use of a solvent.

Methanol in the range of 5 weight % to 15 weight %, preferably 10 weight %, based on the weight of mercaptan charged, is added to the reactor to provide for all of the following improvements: an increased reaction rate; a reduction in the amount of caustic and copper cocatalyst; two phases which separate cleanly at the end of the reaction; the solvent is primarily in the water phase which simplifies the recovery and recycle of the solvent; allows for the removal of unwanted dimethyl sulfide from the system (which comes in with the methyl mercaptan) so that it does not build up in the process; and produces a minimum amount of by-products such as, for example, 2,3,5-trithiahexane.

According to the invention, methyl mercaptan, 20% caustic, a copper salt and methanol are charged to the batch reactor, as described earlier, which is heated to 50° C. and pressured to 400 psig with nitrogen. Oxygen is added to the vapor phase of the reactor on demand with a pressure differential no greater than 20 psig in order to maintain the concentration of oxygen at about 5 volume %. The reactor has sufficient mixing that diffusion of the oxygen into the liquid phases will result in a sufficiently fast reaction that reasonable batch times can be achieved economically.

The catalyst system consists of both a caustic solution and a copper salt. The concentration of the caustic solution range from 5 to 50 weight %, preferably 20 weight %. The caustic solution is added in an amount from 0.5 to 2.5 weight % based on the weight of mercaptan charged to the reactor. The amount of caustic charged is preferably 1.5 to 2.5 weight % based on mercaptan, and the most preferred amount is 2.0 weight %. The other cocatalyst can be salts of copper, cobalt, iron, nickel, chromium as the acetate, sulfate, nitrate, phosphate, chloride or other such salt. The preferred catalyst is copper in the form of the acetate or sulfate, or the hydrated forms thereof. The amount of copper added (weight of metal vs. weight of mercaptan) should be 0.0010% to 0.0100%, preferably from 0.0040 to 0.0060% based on the weight of copper metal to mercaptan.

The invention process provides (1) an optimum reaction rate that is steady throughout the course of reaction; (2) greater than 99.5% conversion of methyl mercaptan; (3) less than 0.10% by-product 2,3,5-trithiahexane; (4) clean phase separation of the aqueous and dimethyl disulfide phases; and (5) a simplified distillation scheme. Distillation of the aqueous phase results in an overhead for recycle to the reactor that contains the majority of the methanol and unreacted methyl mercaptan and dimethyl disulfide that was soluble in the water phase. The distilled aqueous phase kettle contains the diluted caustic which can be neutralized for disposal. The organic phase is greater than 98% dimethyl disulfide and can be recovered in a continuous distillation column at greater than 99.5%, typically >99.8% purity. Finally, a significant portion of the dimethyl sulfide impurity from the methyl mercaptan is removed in the overhead distillation cut of the organic phase along with a small amount of methanol, water and trace amounts of methyl mercaptan.

EXAMPLE 1

The runs were done in a 1 liter autoclave reactor equipped with a variable speed magna drive mixer; an internal coil for heating and cooling; an internal thermowell for monitoring and controlling the temperature; a connection to a pressure transducer for monitoring reaction pressure; a port for charging methyl mercaptan through a dedicated charge line; a port in the head of the reactor for adding the caustic, solvent and cocatalyst or higher boiling mercaptans; a port in the reactor head for introducing the oxygen into the vapor space; a port for venting the reactor contents to the flare either manually or by remote activation of an emergency dump valve; a port for a rupture disk assembly; and a bottom drain valve for emptying the reactor at the end of the run.

Methyl mercaptan was charged to the reactor from a storage cylinder that was placed on a balance and connected to the reactor via flexible stainless steel tubing. The transfer line was connected to a manifold, which allowed transfer of the methyl mercaptan to the reactor or to be vented to the flare line. The manifold also had a connection to a nitrogen source for purging the line after use. Oxygen was introduced to the reactor from a 4 liter vessel initially at about 800–900 psig. The vessel had a pressure transducer which allows for remote monitoring of the pressure on this vessel. The oxygen vessel was connected to the reactor via a pressure regulator to supply oxygen to a motor control valve set at a pressure of 5% over that of the reactor pressure. The flow of oxygen to the reactor was initiated by remote operation of a solenoid valve.

Ten grams of 20% caustic and 50 cc (39.5 grams) of methanol were charged to the autoclave through the top port. The port was sealed and the reactor purged with nitrogen. Methyl mercaptan (384 grams) was added to the reactor through the transfer line. The stirrer was started and set at 1000 rpm. The temperature controller was set at 50° C. and turned on. The controller operated a motor valve that sent steam or chilled water to the reactor. After the temperature reached 50° C., nitrogen was charged to the reactor vapor space to bring the pressure to 400 psig. The oxygen reservoir pressure was read and the solenoid valve was opened to allow oxygen to enter the vapor space of the reactor and the pressure rose to 420 psig. As the oxygen was reacted and the pressure dropped, the motor valve allowed additional oxygen to be fed to the reactor on demand but kept the reactor pressure below 420 psig. The amount of oxygen used was monitored by following the pressure drop on the oxygen vessel which had a calibrated volume so the number of moles of oxygen charged to the reactor can be calculated. After oxygen addition began, the temperature controller went from heating to full cooling to maintain the reaction temperature constant at the set temperature. When the methyl mercaptan was essentially completely converted to dimethyl disulfide, the oxygen addition ceases and the temperature control went from cooling to supplying heat to maintain the reaction temperature. The initial rate of oxygen consumption was 3.8 mmole of oxygen per minute. This rate of oxygen reaction was used as the basis of comparison for the various runs. After about one hour, the reaction rate increased to 7.6 mmole per minute. The reaction was complete (as defined above) in 5.1 hours for an average reaction rate of 6.5 mmole per minute. The reactor temperature was cooled to 25° C., the pressure on the reactor was relieved to the flare line and the vessel purged with nitrogen. The crude product was drained from the reactor through the bottom drain valve. Because residual methyl mercaptan in the sample created a very strong odor, proper precautions were taken to prevent leaks to the atmosphere. The crude product did not separate into two phases but was an obvious emulsion. The addition of 40 cc water resulted in two phases that were separated cleanly, with the aqueous phase on top. GC analysis of the phases indicated that the conversion of methyl mercaptan was 98.7%, with a selectivity to dimethyl disulfide >99.85%. It should be noted that this was not the first run in the reactor that was therefore already preconditioned as will be illustrated in examples 12 through 15. The same equipment and procedure were used in all runs and, unless otherwise noted, the amount of mercaptan charged was 384 grams, even when other mercaptans were used.

EXAMPLE 2

In this example, 60 grams of 33% caustic was used as the catalyst. The initial rate of reaction was 5.5 mmole oxygen per minute. After approximately 50% conversion of the methyl mercaptan, the reaction rate increased to about 10.2 mmole/minute. The reaction was considered complete after 4.6 hours. The crude product phases separated readily with the aqueous phase on bottom. Mercaptan conversion was 99.6% with selectivity to dimethyl disulfide of 99.48%. There was 0.51% selectivity to 2,3,5-trithiahexane.

EXAMPLE 3

The run was carried out by charging 10 grams of 20% caustic, 50 cc (53.9 grams) of dimethyl disulfide and 384 grams of methyl mercaptan to the reactor. The reaction was run at 50° C. and required 2.75 hours to complete. The reaction started out slow but increased with mercaptan conversion to give an average oxygen reaction rate of 12.1 mmole/minute with a maximum rate of 14.4 mmole/minute. At the end of the run, the crude product did not phase separate well. After addition of 2.4 g of sulfuric acid to neutralize the caustic, the phases separated to give 76.5 g of aqueous phase and 435.1 g of organic phase. The methyl mercaptan conversion was 99.3% with a selectivity to dimethyl disulfide of 99.85%.

EXAMPLE 4

The run was carried out by first charging 355 grams of methyl mercaptan, 10 grams of 20% caustic and 0.30 grams of TERGITOL® 15-S-7 to the reactor and the reaction was run at 50° C. The average reaction rate was 10.1 mmole/minute. Once the methyl mercaptan conversion reached about 97%, an additional 35 minutes was required to reach the point the reaction was considered complete. The total reaction time was 3.08 hours. The crude product did not phase separate even after neutralization of the caustic with sulfuric acid. The addition of 50 grams of pentane resulted in clean separation with the aqueous phase on bottom. The mercaptan conversion was only 98.5% while the selectivity to disulfide was 99.75%.

EXAMPLE 5

This run was a combination of examples 3 and 4 in that 384 grams of methyl mercaptan, 53.7 grams dimethyl disulfide, 10 grams of 20% caustic and 0.30 grams of Tergitol 15-S-7 were charged to the reactor. The reaction was run at 50° C. and required 2.17 hours to complete with an average reaction rate of 14.1 mmole/minute. The crude product separated reasonably well but was milky. Separation improved with the addition of pentane to the crude product. The mercaptan conversion was 99.0% with a disulfide selectivity of 99.9%.

EXAMPLE 6

The run was carried out by first charging 384 grams of methyl mercaptan, 10 grams of 20% caustic and 39.5 grams (50 cc) of methanol to the reactor. The reaction was performed at 50° C. and resulted in an average and very steady rate of 27.1 mmole/minute. The crude product separated readily to produce a top aqueous phase, which contained substantially most of the methanol. The conversion of methyl mercaptan was 99.8% with selectivity to disulfide of 99.9%. This example demonstrated the significant improvement in reaction rate obtained by using methanol in the reaction.

EXAMPLE 7

This run was the same as example 6 except that 30 grams of 33% caustic was charged to the reactor along with the methyl mercaptan and methanol. The reaction at 50° C. resulted in a steady reaction rate of 34.7 mmole/minute and a reaction time to completion of 0.92 hours. The crude product phase separated cleanly to give a bottom aqueous phase which contained most of the methanol, but not quite as much as the run with a lower caustic content. The mercaptan conversion was 99.4% and the disulfide selectivity was 99.8% as 0.2% 2,3,5-trithiahexane was produced compared to only 0.1% in the previous example.

EXAMPLE 8

This run was identical to example 6 in the amounts charged to the reactor. However, the reaction temperature was 40° C. The average reaction rate dropped to 20.0 from 27.1 mmole/minute to give a reaction time to completion of 1.67 hours. The separation was clean and the conversion and selectivity were identical to example 6.

EXAMPLE 9

This run was identical to example 6 except that the reaction temperature was 60° C. to give an average reaction rate of 32.8 mmole/minute.

EXAMPLE 10

This example illustrates that triethyl amine could be utilized as a catalyst in this reaction. Thirty grams of triethyl amine, 30 grams of water and 384 grams of methyl mercaptan were reacted with oxygen at 50° C. The average reaction rate was 10.5 mmole/minute, but was not consistent throughout the reaction and slowed at high conversion of mercaptan. The conversion of mercaptan was 99.8% while the disulfide selectivity was 99.4%. The phases separated well with the aqueous phase on top which contained about 15% of the triethyl amine. The organic phase contained predominately the disulfide product as well as about 85% of the charged triethyl amine. Although not illustrated, the addition of water as solvent was important for obtaining reaction rates with triethyl amine that were comparable to those obtained with caustic. Also high charge levels of triethyl amine were required for the faster rates.

EXAMPLE 11

This run was performed to determine if dimethyl sulfide had an impact on the reaction. Dimethyl sulfide is an impurity that can be present, usually in low levels of about 0.05–0.15%, in the methyl mercaptan. First, 384 grams of methyl mercaptan, 10 grams of 20% caustic, 25 cc of methanol and 25 cc of dimethyl sulfide were charged to the reactor. The oxidation was then performed at 50° C. to give an average reaction rate of 9.0 mmole/minute. The reaction rate was slow during most of the run, but increased toward the end. The presence of dimethyl sulfide did not impact the mercaptan conversion or dimethyl disulfide selectivity.

EXAMPLE 12–15

As indicated at the end of example 1, there was a conditioning effect seen on repeated runs. This can be illustrated with this series of runs.

The reactor was rinsed with water and then acetone and then again with distilled water. Then, 3 84 grams of methyl mercaptan, 10 grams of 20% caustic and 50 cc of methanol were charged to the reactor and the oxidation performed at 50° C. The reactor was drained and then recharged for the next three runs in exactly the same manner. The reaction rates and batch times are shown in Table I.

TABLE I

| Example Number | Reaction Time | Average Reaction Rate |
| --- | --- | --- |
| 12 | 1.63 hours | 20.4 mmole/min. |
| 13 | 2.00 hours | 16.7 mmole/min. |
| 14 | 2.62 hours | 12.7 mmole/min. |
| 15 | 2.68 hours | 12.4 mmole/min. |

The results of these examples demonstrate that there was some impact on reaction rate due to a freshly cleaned vessel. Whenever the vessel was cleaned during the course of this study, several runs with our base line case of methanol and caustic were made prior to runs that were made to determine the impact of some change in operating conditions.

EXAMPLE 16

This run was done to test the effect of added metal ions to the reaction, iron in this case. First, 384 grams of methyl mercaptan, 0.10 grams of ferric sulfate pentahydrate dissolved in 50 cc of methanol and 10 grams of 20% caustic were charged to the reactor. A very clean fast oxidation reaction resulted at 50° C. The time to completion was 0.77 hours, corresponding to an average reaction rate of 43.4 mmole/minute. A clean phase separation was obtained. The mercaptan conversion was greater than 99.9% with a disulfide selectivity of 99.85%.

EXAMPLE 17

The run was carried out by charging 384 grams of methyl mercaptan, 10 gram of 4% caustic and 0.10 grams of ferric sulfate pentahydrate dissolved in 50 cc of methanol to the reactor. The oxidation was performed at 50° C. After about 0.83 hours, approximately 51% of the required oxygen was consumed. There was only an additional 2% consumed after an additional 0.50 hours of reaction time. At this point, an additional 8 grams of 20% caustic was charged to the reactor by pressuring this solution into the reactor from a small pressure vessel connected to one of the ports of the reactor. The reaction was finished in an additional 0.40 hours after the addition of more caustic, an amount now equal to that charged in example 16.

EXAMPLE 18

The run was carried out by adding 3 84 grams of methyl mercaptan, 10 grams of 20% caustic, and 0.10 grams of cupric sulfate pentahydrate dissolved in 50 cc of methanol to the reactor. The oxidation was done at 50° C. to give a fast, steady reaction rate of 62.5 mmole/minute and a time to completion of 0.53 hours. The mercaptan conversion was greater than 99.9% with a disulfide selectivity of 99.9%.

EXAMPLE 19

The run was the same as that shown in example 18 except that 10 grams of 4% caustic was used. A slower, but steady reaction rate of 25.0 mmole/minute was obtained. The methyl mercaptan conversion after 1.33 hours was 99.7% with the selectivity to the disulfide at 99.7% as 0.3% of the trithiahexane was produced. This example, when compared to example 17, demonstrates that copper cocatalyst was better than iron at a low caustic content.

EXAMPLE 20

This example is the same as example 18 except that 0.080 grams of cupric acetate monohydrate was used in place of cupric sulfate. The amount of copper on a molar basis is essentially the same in the two runs. The reaction was complete in 0.50 hours to give a reaction rate of 66.7 mmole/minute. The conversion and selectivity were both greater than 99.9%.

EXAMPLES 21–40

To better define the scope of the oxidation reaction using caustic, methanol and copper cocatalyst, a statistically designed experiment of twenty runs were made. The ranges for the charge amounts are shown in Table II.

TABLE II

|  | (−1) | (0) | (+1) |
|---|---|---|---|
| 20% caustic | 2.0 grams | 6.0 grams | 10.0 grams |
| Methanol | 25 cc | 50 cc | 75 cc |
| Copper acetate | 0.020 grams | 0.050 grams | 0.080 grams |

In each run, 384 grams of methyl mercaptan was charged and the oxidation performed at 50° C. The results, including the amount of the other reagents charged, the time to completion, the reaction rate, the amount of unreacted methyl mercaptan and the amount of 2,3,5-trithiahexane produced under each condition, are shown in the following Table III.

TABLE III

| Example | NaOH (g) | MeOH (g) | Cu(OAc)$^2$ (g) | Time (minutes) | Rate (mmol/min) | % MeSH | % Trithia hexane |
|---|---|---|---|---|---|---|---|
| 21 | 2.00 | 25 | 0.020 | 69 | 29.0 | 1.192 | 0.093 |
| 22 | 2.00 | 25 | 0.080 | 90 | 22.2 | 1.050 | 0.152 |
| 23 | 2.00 | 25 | 0.080 | 58 | 34.5 | 1.425 | 0.118 |
| 24 | 2.00 | 75 | 0.020 | 42 | 47.6 | 1.152 | 0.207 |
| 25 | 2.00 | 75 | 0.020 | 48.5 | 41.2 | 1.064 | 0.226 |
| 26 | 10.00 | 25 | 0.020 | 37 | 54.1 | 0.007 | 0.037 |
| 27 | 2.00 | 75 | 0.080 | 52 | 38.5 | 1.132 | 0.271 |
| 28 | 10.00 | 25 | 0.080 | 31 | 64.5 | 0.005 | 0.057 |
| 29 | 10.00 | 75 | 0.020 | 42 | 47.6 | 0.027 | 0.056 |
| 30 | 10.00 | 75 | 0.080 | 32 | 62.5 | 0.097 | 0.058 |
| 31 | 6.00 | 50 | 0.050 | 37 | 54.1 | 0.155 | 0.096 |
| 32 | 6.00 | 50 | 0.050 | 31 | 64.5 | 0.242 | 0.083 |
| 33 | 6.00 | 50 | 0.050 | 39 | 51.3 | 0.117 | 0.066 |
| 34 | 10.00 | 50 | 0.080 | 31 | 64.5 | 0.021 | 0.066 |
| 35 | 2.00 | 50 | 0.050 | 40.4 | 49.4 | 1.272 | 0.215 |
| 36 | 10.00 | 50 | 0.050 | 30 | 66.6 | 0.028 | 0.051 |
| 37 | 6.00 | 25 | 0.050 | 42.5 | 47.0 | 0.081 | 0.063 |
| 38 | 6.00 | 75 | 0.050 | 37 | 54.0 | 0.474 | 0.077 |
| 39 | 6.00 | 50 | 0.020 | 42.5 | 47.0 | 0.342 | 0.092 |
| 40 | 6.00 | 50 | 0.080 | 31 | 64.5 | 0.092 | 0.079 |

The regression analysis of the data in Table III using the normalized values for the variables (−1 for low value, 0 for mid-range value, +1 for high value) and a full quadratic fit gave the results shown in Table IV. The reaction rate was most influenced by the caustic and copper concentrations. The fact that there was a negative interaction term involving caustic and methanol and methanol itself caused curvature in the data. The result demonstrates that best overall rates were obtained when copper and caustic were high and fell off as either or both were lowered. This effect was least at high methanol content, but was very pronounced at low methanol content. The optimum amount of methanol for reaction rate was the mid-range to high value. The amount of residual MeSH was most impacted by the caustic concentration, with high caustic preferred to minimize residual MeSH. The methanol and copper concentration had little impact on the residual MeSH. The amount of trihiahexane was minimized at low methanol and high caustic concentration. The copper content had very little impact on the amount of trihiahexane.

TABLE IV

Regression Analysis Using Normalized Data (−1, 0, +1)

| Terms | Reaction Rate | % Residual MeSH | % 2,3,5-Trithiahexane |
|---|---|---|---|
| Intercept | +55.451 | +0.2057 | +0.0846 |
| (NaOH) | +8.5555 | −0.5942 | −0.06553 |
| (MeOH) | +2.79 | +0.0128 | +0.0311 |
| (Cu) | +4.8455 | +0.0098 | +0.008775 |
| (NaOH)*(MeOH) | −4.7375 | +0.06113 | −0.03213 |
| (NaOH)*(Cu) | +1.4693 | −0.02075 | −0.007157 |
| (MeOH)*(Cu) | +0.3875 | −0.0171 | +0.001375 |
| (NOH)*(NaOH) | +0.187 | +0.4152 | +0.04653 |
| (MeOH)*(MeOH) | −5.34 | +0.03118 | −0.01635 |
| (Cu)*(Cu) | −2.063 | −0.0178 | −0.0009745 |

EXAMPLES 41–60

These examples illustrate the oxidation of various mercaptans to their corresponding disulfide by charging 10 grams of 20% caustic, 50 cc methanol, 384 grams of the mercaptan and the amount of metal salt such that all were tested had the same molar amount of metal as contained in 0.100 grams of copper sulfate pentahydrate. The oxidation reactions were all run at 50° C. and 5 volume % oxygen at 400 psig reactor pressure. Table V compares the average reaction rate in mmole oxygen reacted per minute for the various mercaptans and copper, cobalt, or nickel salts tested. Blank spaces in Table V indicate that no tests were done. Table V also shows that, with a given cocatalyst, methyl mercaptan had the highest reaction rate.

TABLE V

| | Rate (mmol/min) | | | | | |
|---|---|---|---|---|---|---|
| Cocatalyst | none | $CuCl_2$ | $CuAc_2$ | $CuSO_4$ | $CoCl_2$ | $CoAc_2$ | $NiCl_2$ |
| MeSH | 10.9 | 60.6 | 66.7 | 62.5 | 47.6 | | |
| EtSH | 4.0 | 43.0 | 49.9 | 46.9 | 3.0 | 12.3 | 15.0 |
| n-PrSH | | 31.9 | | 33.6 | 13.9 | | |
| iso-PrSH | | 21.8 | | | 21.8 | | |
| sec-BuSH | 1.5 | 18.4 | | 15.0 | 32.2 | | |

EXAMPLES 61–67

These examples demonstrate the importance of mixing and oxygen partial pressure on the reaction rate using 384 grams of ethyl mercaptan, 10 grams of 20% caustic, 50 cc of methanol and 0.050 grams cupric acetate monohydrate, except in example 67 where no copper was added to the reaction mixture. Ethyl mercaptan was used in each run. The stirrer speed used was 300, 700 or 1000 rpm and the oxygen volume % was either 3% or 5%. The results are shown in Table VI.

TABLE VI

| Example | RPM | % Oxygen | Relative Reaction Rate |
|---|---|---|---|
| 61 | 1000 | 5 | 57.3 |
| 62 | 1000 | 3 | 29.2 |
| 63 | 700 | 5 | 32.3 |
| 64 | 700 | 3 | 23.8 |
| 65 | 300 | 5 | 9.0 |
| 66 | 300 | 3 | 6.5 |
| 67 | 700 | 3 | 5.6 (No Copper) |

EXAMPLE 68

Ten of the products produced in Examples 21–40 were combined. The following Tables VII and VIII illustrate the charge to the reactor and the composition of the combined crude after reaction and the distribution of material in the phases.

TABLE VII

| Reactor Charge | | | Crude Product | |
|---|---|---|---|---|
| Moles | Weight (g) | Chemical | Moles | Weight (g) |
| 80.0000 | 3840.0 | Methyl mercaptan | 0.3020 | 14.5 |
| 0.1129 | 7.0 | Dimethylsulfide | 0.1129 | 7.0 |
| 7.8125 | 250.0 | Methanol | 7.8125 | 250.0 |
| 0.4500 | 18.0 | Sodium hydroxide | 0.4500 | 18.0 |
| 4.0000 | 72.0 | Water | 43.8245 | 788.8 |
| 19.9123 | 637.2 | Oxygen | | |
| | | Dimethyl Disulfide | 39.7755 | 3738.9 |
| | | 2,3,5-trithiahexane | 0.0490 | 6.9 |
| Total | 4824.2 | | | 4824.1 |

TABLE VIII

| | Distribution of Phases | | |
|---|---|---|---|
| Chemical | Organic | Aqueous | Vapor |
| Methyl mercaptan | 4.5 | 6.5 | 3.5 |
| Dimethylsulfide | 6.0 | 1.0 | |
| Dimethyl disulfide | 3735.8 | 3.1 | |
| Trithiahexane | 5.4 | 1.5 | |
| Water | 5.8 | 783.0 | |
| Methanol | 22.5 | 227.5 | |
| Sodium hydroxide | 0.1 | 17.9 | |
| Total | 3780.0 | 1040.6 | 3.5 |

In a batch distillation of the organic phase, 3660.8 grams or 95.3% of the contained dimethyl disulfide was obtained as greater than 99.8% pure material, 3.0% of the organic phase was taken overhead and contained substantially all of the dimethylsulfide, water, unreacted methyl mercaptan, and 2.0% of the contained dimethyl disulfide. This stream could be sent to a slop stream for returning to a refinery stream or for other treatment. This stream contained most of the unwanted dimethyl sulfide that entered as an impurity in the methyl mercaptan. By not returning this overhead to the reactor, the build up of dimethylsulfide can be avoided. The dimethyl disulfide that was lost overhead was due to the water/dimethyl disulfide azeotrope. Approximately 75% of the copper present originally as copper acetate was in the organic phase. After the distillation, the copper was in the form of insoluble copper sulfide, oxide and/or hydroxide. Less than 1 ppm of copper was detected in solution. No copper was detected in the overhead dimethyl disulfide product.

The aqueous phase was distilled to take overhead essentially all of the methanol that was contained in this phase or 91% of the total methanol employed in the reaction. The overhead also contained unreacted methyl mercaptan, dimethylsulfide and all of the dimethyl disulfide that was present in the aqueous phase. The kettle contained essentially all of the sodium hydroxide and the 2,3,5-trithiahexane and 25% of the original amount of copper in the crude reactor product was present as an insoluble flocculent material. The amount of copper present in solution after the distillation was less than 1 ppm.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the specification and the claims.

That which is claimed is:

1. A process for producing organic disulfide consisting essentially of:
   (A) introducing oxygen into an oxygen-containing fluid in a vapor phase of a reaction zone containing a liquid phase and said vapor phase;
   (B) contacting said oxygen with a basic catalyst and a mercaptan;
   (C) maintaining the reaction chamber at a temperature in the range of about 10° C. to about 200° C. and a pressure in the range of about 1 atm to about 100 atm and
   (D) maintaining the oxygen content in the vapor phase in a range of up to about 8 volume percent until the mercaptan is essentially converted to organic disulfide.

2. A process according to claim 1 wherein said basic catalyst is selected from the group consisting of inorganic base, organic base, and combinations thereof.

3. A process according to claim 3 wherein said basic catalyst is selected from the group consisting of methyl amine, dimethyl amine, trimethyl amine, ethyl amine, diethyl amine, triethylamine, propyl amine, isopropyl amine, dipropyl amine, diisopropyl amine, tripropyl amine, butyl amine, tributyl amine, amyl amine, triamyl amine, hexyl amine, cyclohexyl amine, octyl amine, tetramethylammonium hydroxide, tetraethylammonium hydroxide, piperindine, pyrrolidine, morpholine, dimethylethanol amine, tetrapropylammonium hydroxide, lithium hydroxide, sodium hydroxide, sodium hydrosulfide, sodium bisulfide, potassium hydroxide, calcium hydroxide, magnesium hydroxide, sodium bicarbonate, sodium carbonate, sodium oxide, sodium sulfide, magnesium oxide, calcium oxide, calcium carbonate, sodium phenoxide, barium phenoxide, calcium phenoxide, partially neutralized acids in which one or more protons of an acid is replaced with ammonium or metal ions, $R^1ONa$, $R^1OK$, $R^1SNa$, $R^1SK$, and combinations of two or more thereof wherein $R^1$ is a $C_1$–$C_{18}$ alkyl radical, or combinations of two or more thereof.

4. A process according to claim 1 wherein said basic catalyst is selected from the group consisting of triethylamine, sodium hydroxide, and combinations thereof.

5. A process according to claim 1 wherein said reaction medium further comprises a cocatalyst which is a transition metal or transitional metal compound.

6. A process according to claim 5 wherein said cocatalyst is selected from the group consisting of ferric chloride, ferric bromide, ferric sulfate, ferric nitrate, ferric phosphate, cobalt chloride, cobalt bromide, cobalt sulfate, cobalt nitrate, cobalt phosphate, nickel chloride, nickel bromide, nickel sulfate, nickel nitrate, nickel phosphate, copper chloride, copper bromide, copper sulfate, copper nitrate, copper phosphate, copper acetate, cobalt acetate, nickel acetate, copper naphthenate, cobalt naphthenate, nickel naphthenate, copper oxide, copper hydroxide, nickel oxide, nickel hydroxide, cobalt oxide, or combinations of two or more thereof.

7. A process according to claim 5 wherein said basic catalyst is triethylamine.

8. A process according to claim 5 wherein said basic catalyst is sodium hydroxide.

9. A process according to claim 5 wherein said cocatalyst is a copper salt.

10. A process according to claim 7 wherein said cocatalyst is a copper salt.

11. A process according to claim 8 wherein said cocatalyst is a copper salt.

12. A process according to claim 1 wherein said reaction medium further comprises a solvent.

13. A process according to claim 11 wherein said reaction medium further comprises a solvent.

14. A process according to claim 1 wherein said mercaptan is methyl mercaptan.

15. A process according to claim 13 wherein said mercaptan is methyl mercaptan.

16. A process for producing organic disulfide consisting essentially of:
   (A) introducing oxygen into an oxygen-containing fluid in a vapor phase of a reaction zone containing a liquid phase and said vapor phase;
   (B) contacting said oxygen with a basic catalyst, a cocatalyst, a solvent, and a mercaptan;
   (C) maintaining the reaction chamber at a temperature in the range of about 10° C. to about 200° C. and a pressure in the range of about 1 atm to about 100 atm and
   (D) maintaining the oxygen content in the vapor phase in a range of up to about 8 volume percent until the mercaptan is essentially converted to organic disulfide; wherein
   said basic catalyst is selected from the group consisting of inorganic base, organic base, and combinations thereof; and
   said cocatalyst is a transition metal or transitional metal compound.

17. A process according to claim 16 wherein
   said basic catalyst is selected from the group consisting of methyl amine, dimethyl amine, trimethyl amine, ethyl amine, diethyl amine, triethylamine, propyl amine, isopropyl amine, dipropyl amine, diisopropyl amine, tripropyl amine, butyl amine, tributyl amine, amyl amine, triamyl amine, hexyl amine, cyclohexyl amine, octyl amine, tetramethylammonium hydroxide, tetraethylammonium hydroxide, tetrapropylammonium hydroxide, lithium hydroxide, sodium hydroxide, sodium hydrosulfide, sodium bisulfide, potassium hydroxide, calcium hydroxide, magnesium hydroxide, sodium bicarbonate, sodium carbonate, sodium oxide, sodium sulfide, magnesium oxide, calcium oxide, calcium carbonate, sodium phenoxide, barium phenoxide, calcium phenoxide, partially neutralized acids in which one or more protons of an acid is replaced with ammonium or metal ions, $R^1ONa$, $R^1OK$, $R^1SNa$, $R^1SK$, and combinations of two or more thereof where $R^1$ is a $C_1$–$C_{18}$ alkyl radical, or combinations of two or more thereof; and said cocatalyst is selected from the group consisting of ferric chloride, ferric bromide, ferric sulfate, ferric nitrate, ferric phosphate, cobalt chloride, cobalt bromide, cobalt sulfate, cobalt nitrate, cobalt phosphate, nickel chloride, nickel bromide, nickel sulfate, nickel nitrate, nickel phosphate, copper chloride, copper bromide, copper sulfate, copper nitrate, copper phosphate, copper sulfate, copper acetate, cobalt acetate, nickel acetate, copper naphthenate, cobalt naphthenate, nickel naphthenate, copper oxide, copper hydroxide, nickel oxide, nickel hydroxide, cobalt oxide, or combinations of two or more thereof.

18. A process according to claim 16 wherein said basic catalyst is selected from the group consisting of triethylamine, sodium hydroxide, and combinations thereof, said solvent is methanol, and said cocatalyst is a copper salt.

19. A process according to claim 18 wherein the oxygen concentration in said vapor phase is about 5 volume %, said basic catalyst is present in said reaction medium in the range of 1.5 to 2.5 weight % based on the weight of said mercaptan, and said solvent is present in the range of 0.005 to 5 weight % of said reaction medium.

20. A process for producing dimethyl sulfide consisting essentially of:
   (A) introducing oxygen into an oxygen-containing fluid in a vapor phase in a reaction zone comprising said vapor phase and a liquid phase;
   (B) contacting said oxygen with a reaction mixture which comprises methyl mercaptan, methanol, a copper salt, and a base selected from the group consisting of triethylamine, sodium hyroxide, and combinations thereof, to produce in said liquid phase a product mixture comprising an aqueous phase and an organic phase;
   (C) maintaining the reaction chamber at a temperature in the range of about 10° C. to about 200° C. and a pressure in the range of about 1 atm to about 100 atm;
   (D) maintaining the oxygen content in the vapor phase in a range of up to about 8 volume percent until the mercaptan is essentially converted to organic disulfide and
   (E) separating said organic phase from said aqueous phase.

21. A process according to claim 20 wherein the oxygen concentration in said vapor phase is about 5% by volume and said base is sodium hydroxide and is present in an amount in the range of 1.5 to 2.5 weight %, based on said methyl mercaptan.

* * * * *